(12) United States Patent
Chodkowski

(10) Patent No.: US 10,821,252 B2
(45) Date of Patent: Nov. 3, 2020

(54) NASAL PILLOW AND PATIENT INTERFACE INCLUDING THE SAME

(71) Applicant: KONINKLIJKE PHILIPS N.V., Eindhoven (NL)

(72) Inventor: Lauren Patricia Chodkowski, Pittsburgh, PA (US)

(73) Assignee: Koninklike Philips N.V., Eindhoven (NL)

( * ) Notice: Subject to any disclaimer, the term of this patent is extended or adjusted under 35 U.S.C. 154(b) by 463 days.

(21) Appl. No.: 15/507,797

(22) PCT Filed: Aug. 20, 2015

(86) PCT No.: PCT/IB2015/056313
§ 371 (c)(1),
(2) Date: Mar. 1, 2017

(87) PCT Pub. No.: WO2016/034970
PCT Pub. Date: Mar. 10, 2016

(65) Prior Publication Data
US 2017/0291003 A1  Oct. 12, 2017

Related U.S. Application Data

(60) Provisional application No. 62/045,216, filed on Sep. 3, 2014.

(51) Int. Cl.
*A61M 16/06* (2006.01)

(52) U.S. Cl.
CPC .... *A61M 16/0666* (2013.01); *A61M 16/0616* (2014.02); *A61M 2210/0618* (2013.01)

(58) Field of Classification Search
CPC .......... A61M 16/0616; A61M 16/0672; A61M 16/0677; A61M 2210/0618; A61M 16/06; A61M 16/0666; A61M 16/105; A61M 15/08
See application file for complete search history.

(56) References Cited

U.S. PATENT DOCUMENTS

| | | | | |
|---|---|---|---|---|
| 4,782,832 | A * | 11/1988 | Trimble | A61M 16/0666 128/204.18 |
| 2002/0069178 | A1* | 6/2002 | Hoffman | G06Q 20/04 705/64 |
| 2006/0283461 | A1 | 12/2006 | Lubke | |
| 2009/0044808 | A1* | 2/2009 | Guney | A61M 16/0825 128/206.24 |
| 2011/0284001 | A1 | 11/2011 | Tero | |
| 2012/0204870 | A1* | 8/2012 | McAuley | A61M 16/0616 128/203.12 |
| 2012/0318274 | A1 | 12/2012 | Ho | |
| 2013/0172759 | A1 | 7/2013 | Melker | |

FOREIGN PATENT DOCUMENTS

| | | | | |
|---|---|---|---|---|
| CN | 101455871 A | | 6/2009 | |
| WO | WO-2014035261 A1 | * | 3/2014 | ........ A61M 16/0875 |
| WO | WO2014035261 A1 | | 3/2014 | |

* cited by examiner

*Primary Examiner* — Samchuan C Yao
*Assistant Examiner* — Nathan M Le
(74) *Attorney, Agent, or Firm* — Michael W. Haas

(57) ABSTRACT

A nasal pillow adapted for use with a patient interface device, the nasal pillow including an outer casing structured to define an interior area; and an inner support structure disposed in the interior area, wherein a rigidity of the inner support structure is greater than a rigidity of the outer casing.

11 Claims, 4 Drawing Sheets

NASAL PILLOW AND PATIENT INTERFACE INCLUDING THE SAME

CROSS-REFERENCE TO RELATED APPLICATIONS

This patent application claims the priority benefit under 35 U.S.C. § 371 (e) of international patent application no. PCT/IB2015/056313, filed Aug. 20, 2015, which claims the priority benefit under 35 U.S.C. § 119(e) of U.S. Provisional Application No. 61/045,216 filed on Sep. 3, 2014, the contents of which are herein incorporated by reference.

BACKGROUND OF THE INVENTION

1. Field of the Invention

The present invention pertains to patient interface devices for delivering a flow of breathing gas to a patient during, for example, respiratory therapy, and, in particular, to nasal pillows adapted for use with patient interface devices.

2. Description of the Related Art

Obstructive sleep apnea (OSA) is a condition that affects millions of people from around the world. OSA is characterized by disturbances or cessation in breathing during sleep. OSA episodes result from partial or complete blockage of airflow during sleep that lasts at least 10 seconds and often as long as 1 to 2 minutes. In a given night, people with moderate to severe apnea may experience complete or partial breathing disruptions as high as 200-500 per night. Because their sleep is constantly disrupted, they are deprived of the restorative sleep necessary for efficient functioning of body and mind. This sleep disorder has also been linked with hypertension, depression, stroke, cardiac arrhythmias, myocardial infarction and other cardiovascular disorders. OSA also causes excessive tiredness.

One method for treating OSA is positive airway pressure (PAP) therapy. Known PAP therapies include continuous positive airway pressure (CPAP), wherein a constant positive airway pressure is provided to the airway of the patient in order to splint the patient's airway open, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient.

FIGS. 1A and 1B show a conventional nasal pillow 1 that is used by some types of patient interface devices. The nasal pillow 1 is partially inserted into a patient's nostril to form a seal with the patient. As shown in FIG. 1A, the nasal pillow 1 has a cone shape. As the nasal pillow 1 is inserted further into the patient's nostril, the nasal pillow 1 comes into contact with the edges of the patient's nostril. The edges of the patient's nostril apply pressure downward and inward on the nasal pillow 1 which forms a seal between the nasal pillow 1 and the patient. However, at the same time, the pressure causes the nasal pillow 1 to collapse and deform. For example, FIG. 1B shows a top view of nasal pillow 1 when downward and inward pressure is applied to it. As shown in FIG. 1B, the opening of nasal pillow 1 is deformed due to the pressure. This deformation can restrict the amount of air that flows through the nasal pillow 1.

SUMMARY OF THE INVENTION

Accordingly, it is an object of the present invention to provide a patient interface device that overcomes the shortcomings of conventional nasal pillows and patient interface devices. This object is achieved according to one embodiment of the present invention by providing a nasal pillow adapted for use with a patient interface device, wherein the nasal pillow includes an outer casing and an inner support structure having a higher rigidity than the outer casing.

In one embodiment, a nasal pillow adapted for use with a patient interface device includes an outer casing structured to define an interior area; and an inner support structure disposed in the interior area, wherein a rigidity of the inner support structure is greater than a rigidity of the outer casing.

In another embodiment, a patient interface device includes a nasal pillow including an outer casing structured to define an interior area and an inner support structure disposed in the interior area, wherein a rigidity of the inner support structure is greater than a rigidity of the outer casing.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1A:
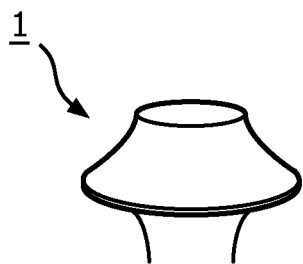
FIG. 1A is a front view of a conventional nasal pillow.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein. As used herein, the word "unitary" means a component is created as a single piece or unit. That is, a component that includes pieces that are created separately and then coupled together as a unit is not a "unitary" component or body.

A system 2 adapted to provide a regimen of respiratory therapy to a patient according to one exemplary embodiment of the disclosed concept is generally shown in FIG. 1. System 2 includes a pressure generating device 4, a delivery conduit 6, and a patient interface device 8. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8. Delivery conduit 6 and patient interface device 8 are typically collectively referred to as a patient circuit.

In the present embodiment, patient interface device 8 includes tubular headgear 10. Tubular headgear 10 is made of hollow tubing that is functional to communicate breathing gas to and from the patient. Tubular headgear 10 is also functional as headgear to attach patient interface device 8 to the patient.

Patient interface device 8 also includes nasal pillows 12. Nasal pillows 12 are structured to fit against the patient's nostrils and form a seal between the patient and patient interface device 8 when patient interface device 8 is worn by the patient. Breathing gas is communicated from the patient to tubular headgear 10 through nasal pillows 12 and vice versa.

Figure 2:
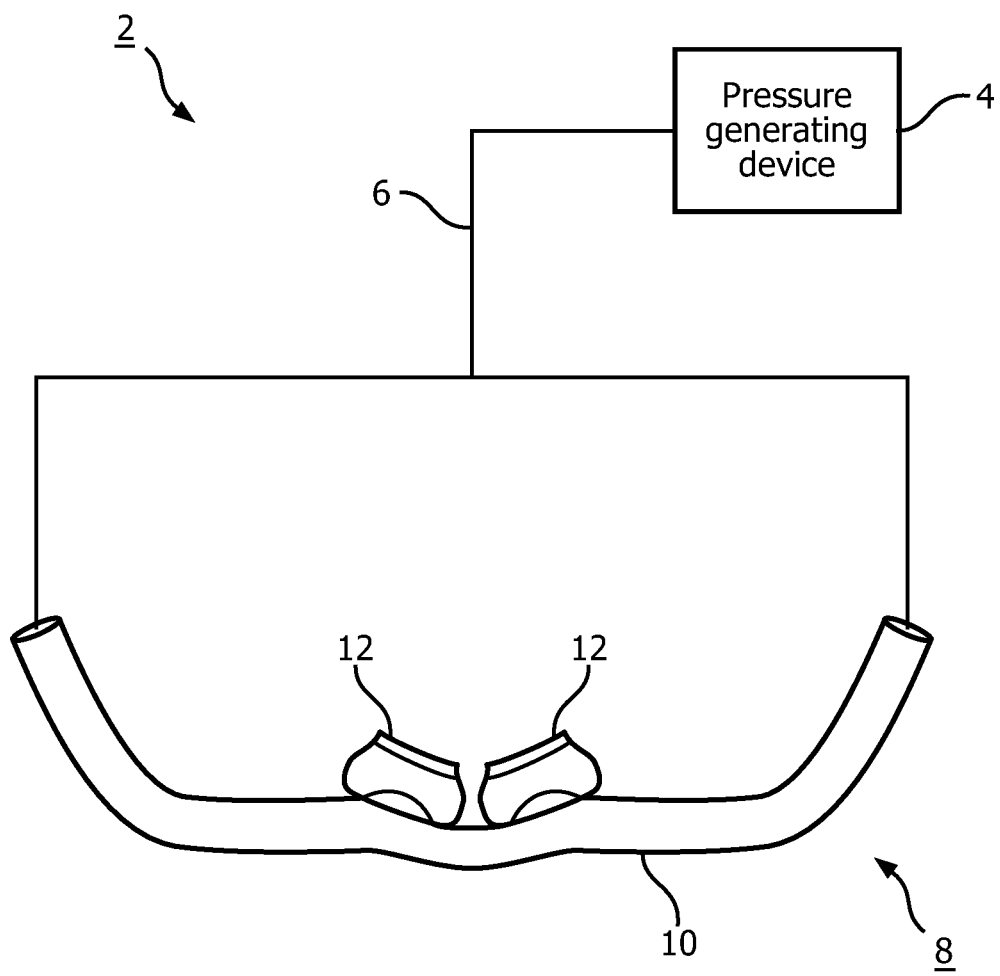
FIG. 2 is a partial schematic diagram of a system adapted to provide a regimen of respiratory therapy to a patient according to an exemplary embodiment of the disclosed concept.

A top view of patient interface device 8 is shown in FIG. 2. As shown more clearly in FIG. 2, tubular headgear 10 is hollow inside to allow it to communicate breathing gas to and from the patient.

Figure 3:
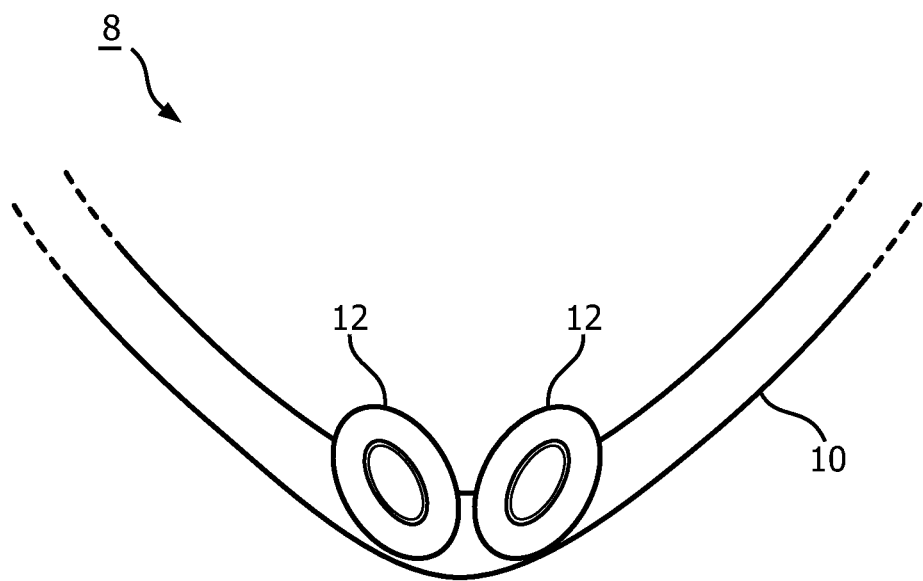
FIG. 3 is a top view of a patient interface device in accordance with an exemplary embodiment of the disclosed concept.

A cross-sectional view of one of the nasal pillows 12 is shown in FIG. 3 in accordance with an exemplary embodiment of the disclosed concept. Nasal pillow 12 has a two-part design including an outer casing 20 and an inner support structure 22. Outer casing 20 forms an exterior shape of nasal pillow 12 and defines an interior area of nasal pillow 12. Outer casing 20 may be made of any suitable material, such as gel, silicone, foam, rubber, or a combination of materials. In one exemplary embodiment, outer casing 20 is made from silicone.

Inner support structure 22 is disposed inside the interior area defined by outer casing 20. In the exemplary embodiment of the disclosed concept shown in FIG. 4, inner support structure 22 has a ring shape. Inner support structure 22 may be made of any suitable material, such as gel, silicone, foam, rubber, or a combination of such materials.

Inner support structure 22 has a rigidity that is higher than a rigidity of outer casing 20. In one exemplary embodiment of the disclosed concept inner support structure 22 has a durometer of a least about 40 shore A and outer casing 20 has a durometer within a range of about 5 shore A to about 20 shore A. Inner support structure 22 with a higher durometer allows nasal pillow 12 top provide rigid and compact support. Also, outer casing 20 with a lower durometer allows nasal pillow 12 to inflate more easily.

Outer casing 20 includes an upper opening 24 and a lower opening 26 that are configured to allow breathing gas to pass from the upper side of outer casing 20 to the lower side of outer casing 20 through outer casing 20. Inner support structure 22 also includes an upper opening 28 and a lower opening 30 which allow gas to pass from the upper side of inner support structure 22 to the lower side of inner support structure 22 through inner support structure 22. Upper openings 24, 28 of outer casing 20 and inner support structure 22 are aligned with each other and lower openings 26, 30 of outer casing 20 and inner support structure 22 are also aligned with each other. As such, breathing gas is able to pass through nasal pillow 12.

Figure 1B:
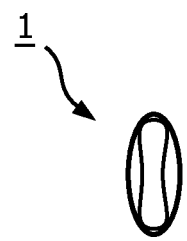
FIG. 1B is a top view of the conventional nasal pillow of FIG. 1A.

Outer casing 20 further includes nasal contact surfaces 32. Nasal contact surfaces 32 are structured to make relatively flush contact with the sub-nasal surface (i.e., the relatively flat area at the bottom of the nostril) of the patient when patient interface device 8 is worn. Nasal pillow 12 also includes base portion 33 which forms a lower part of nasal pillow 12 and is structured to interface nasal pillow 12 with patient interface device 8. Nasal contact surfaces 32 are arranged substantially parallel with base portion 33. However, the disclosed concept is not limited thereto. Nasal contact surfaces 32 may also be arranged at an angle with respect to base portion 33, as will be described in more detail with respect to FIG. 5. When nasal pillow 12 is pressed against or released from the patient, nasal pillow 12 compresses or expands in the directions of arrow 34. Lateral pressure is not put on upper opening 24, so upper opening 24 remains open and allows gas to flow therethrough. In contrast, lateral pressure placed on nasal pillow 1 of FIGS. 1A and 1B causes the opening of nasal pillow 1 to close, as shown in FIG. 1B, thus restricting the flow of gas therethrough.

It is contemplated that various modifications may be made to nasal pillow 12 without departing from the scope of the disclosed concept. Some additional exemplary embodiments of the disclosed concept are shown in FIGS. 5-9 and will be described in more detail hereinafter.

Figure 5:
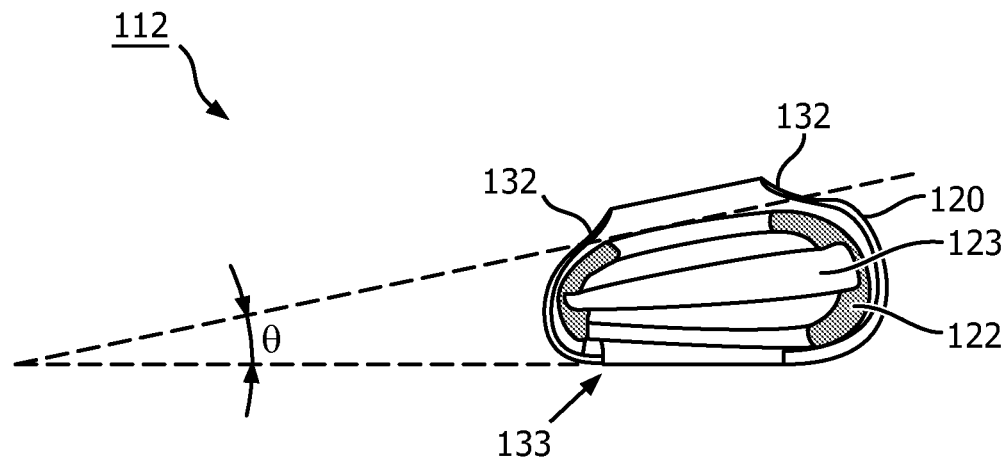
FIG. 5 is a cross-sectional view of a nasal pillow in accordance with another exemplary embodiment of the disclosed concept.

A nasal pillow 112 in accordance with an exemplary embodiment of the disclosed concept is shown in FIG. 5. It is contemplated that nasal pillow 112 may be used in conjunction with the patient interface device 8 shown in FIGS. 2 and 3, or with any other suitable patient interface device.

Nasal pillow 112 includes an outer casing 120 and an inner support structure 122. Outer casing 120 defines an exterior shape of nasal pillow 112 and includes nasal contact surfaces 132. Inner support structure 122 is disposed inside of outer casing 120. Outer casing 120 and inner support structure 122 are pre-loaded. That is, nasal contact surfaces 132 are disposed at an angle θ with respect to a base portion 133 of nasal pillow 112. In contrast, nasal pillow 12 of FIG. 4 includes nasal contact surfaces 32 that are disposed relatively parallel with base portion 33 of nasal pillow 12. Pre-loading outer casing 120 and inner support structure 122 allows nasal pillow 112 to better fit a different shaped nostril.

Inner support structure 122 includes a bellows portion 123 having a single bellows. However, it is contemplated that that any number of bellows may be employed without departing from the scope of the disclosed concept. Bellows portion 123 allows inner support structure 122 to provide additional support to outer casing 120.

Figure 6:
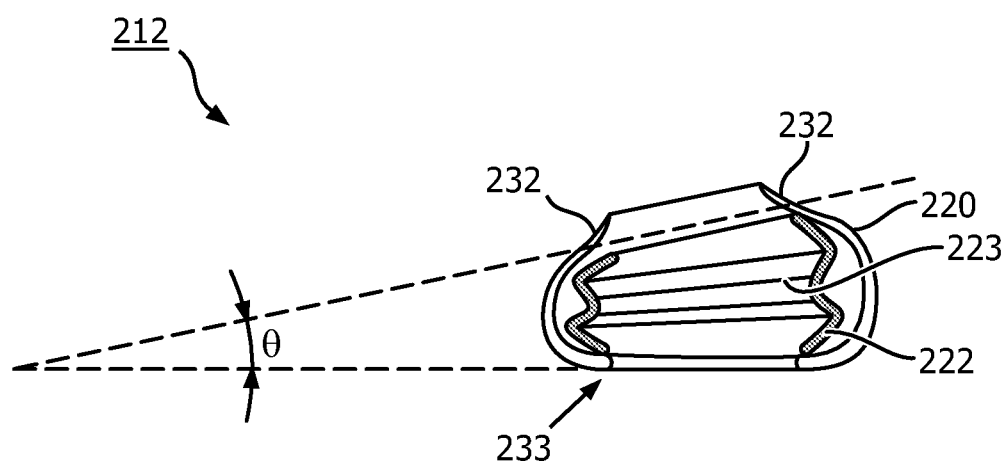
FIG. 6 is a cross-sectional view of a nasal pillow in accordance with another exemplary embodiment of the disclosed concept.

A nasal pillow 212 in accordance with another exemplary embodiment of the disclosed concept is shown in FIG. 6. It is contemplated that nasal pillow 212 may be used in conjunction with the patient interface device 8 shown in FIGS. 2 and 3, or with any other suitable patient interface device.

Nasal pillow 212 includes an outer casing 220 and an inner support structure 222. Outer casing 220 defines an exterior shape of nasal pillow 212 and includes nasal contact surfaces 232. Inner support structure 222 is disposed inside of outer casing 220. Outer casing 220 and inner support structure 222 are pre-loaded to be disposed at an angle θ with respect to a base portion 233 of nasal pillow 212.

Inner support structure 222 includes a bellows portion 223. In contrast bellows portion 123 of inner support structure 122 shown in FIG. 5, bellows portion 223 includes multiple bellows. Bellows portion 223 allows inner support structure 222 to provide additional support to outer casing 220.

Figure 7:
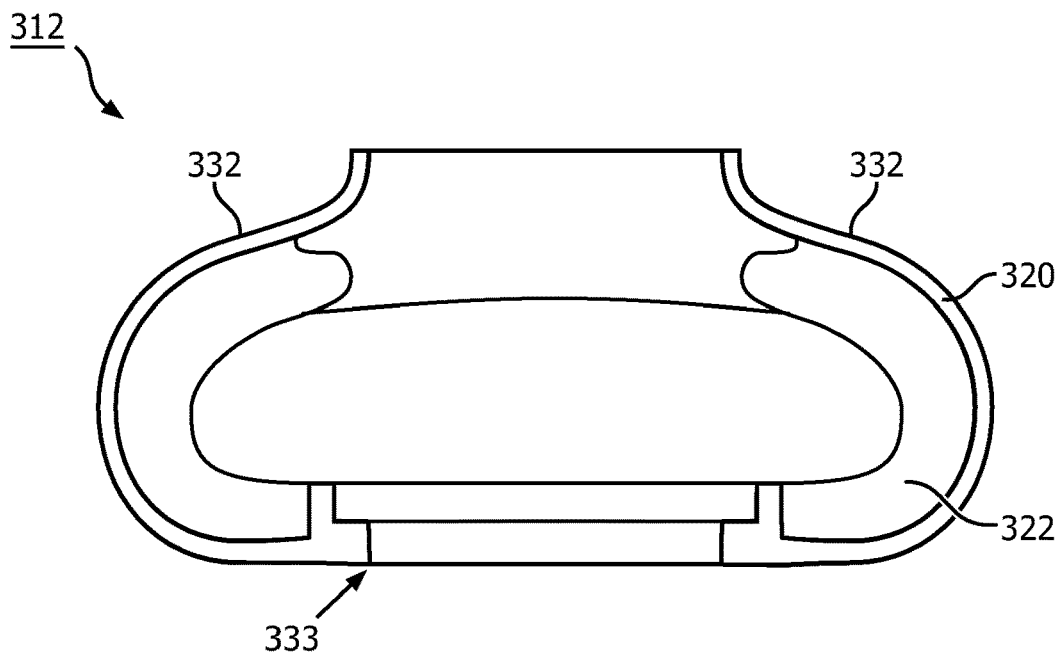
FIG. 7 is a cross-sectional view of a nasal pillow in accordance with another exemplary embodiment of the disclosed concept.

A nasal pillow 312 in accordance with yet another exemplary embodiment of the disclosed concept is shown in FIG. 7. It is contemplated that nasal pillow 312 may be used in conjunction with the patient interface device 8 shown in FIGS. 2 and 3, or with any other suitable patient interface device.

Figure 4:
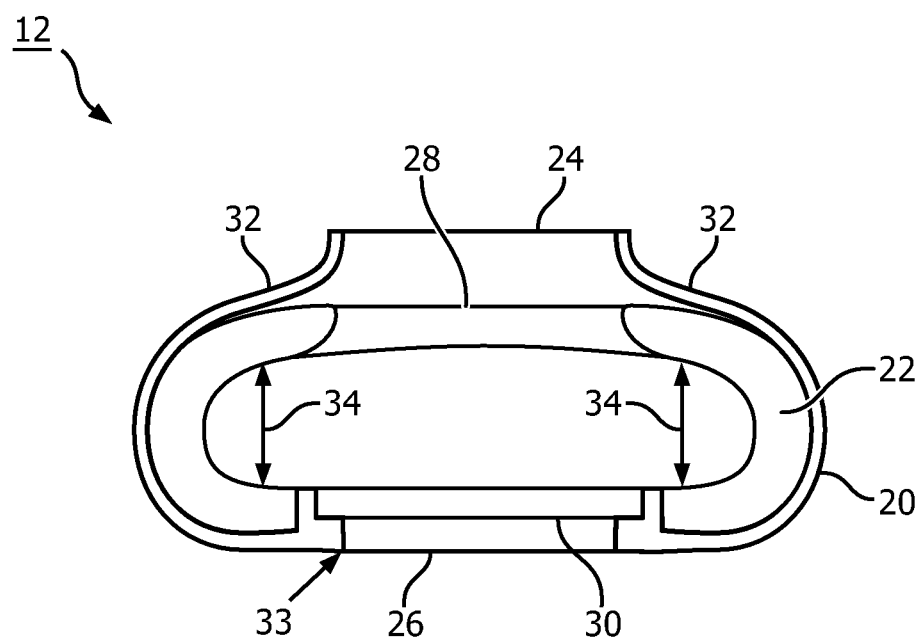
FIG. 4 is a cross-sectional view of a nasal pillow in accordance with an exemplary embodiment of the disclosed concept.

Nasal pillow 312 includes an outer casing 320 and an inner support structure 322 similar to nasal pillow 12 shown in FIG. 4. Nasal pillow 312 also includes nasal contact surfaces 332 that are arranged substantially parallel with a base portion 333 of nasal pillow 312. In contrast with nasal pillow 12 of FIG. 4, in nasal pillow 312 of FIG. 7, outer casing 320 and inner support structure 322 are a unitary object rather than two separate pieces. Outer casing 320 may be overmolded onto inner support structure 322 to create a unitary object. Outer casing 320 may have a different durometer than inner support structure 322. For example, in some exemplary embodiments of the disclosed concept, outer casing 320 has a durometer within a range of about 5 shore A to about 20 shore A and inner support structure 322 has a durometer within a range of about 20 shore A to about 60 shore A. The lower durometer of outer casing 320 provides a softer and more inflatable interface while the higher durometer of inner support structure 322 provides additional support. Outer casing 320 and inner support structure 322 may be made of the same material (e.g., without limitation, silicone) or they may be made of different materials.

Figure 8:
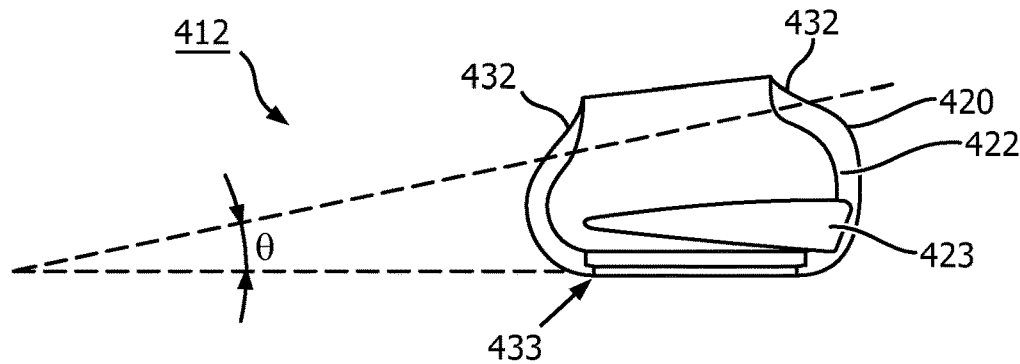
FIG. 8 is a cross-sectional view of a nasal pillow in accordance with another exemplary embodiment of the disclosed concept.

A nasal pillow 412 in accordance with yet another exemplary embodiment of the disclosed concept is shown in FIG. 8. It is contemplated that nasal pillow 412 may be used in conjunction with the patient interface device 8 shown in FIGS. 2 and 3, or with any other suitable patient interface device.

Nasal pillow 412 includes an outer casing 420 and an inner support structure 422. Nasal pillow 412 also includes nasal contact surfaces 432 and a bellows portion 423 having a single bellows. Similar to the nasal pillow 112 of FIG. 5, outer casing 420 and inner support structure 422 of nasal pillow 412 are pre-loaded so that nasal contact surfaces 432 are disposed at an angle θ with respect to a base portion 433 of nasal pillow 412.

In contrast with nasal pillow 112 of FIG. 5, outer casing 420 and inner support structure 422 are a unitary object rather than two separate pieces. Outer casing 420 may be overmolded onto inner support structure 422 to create the unitary object.

Figure 9:
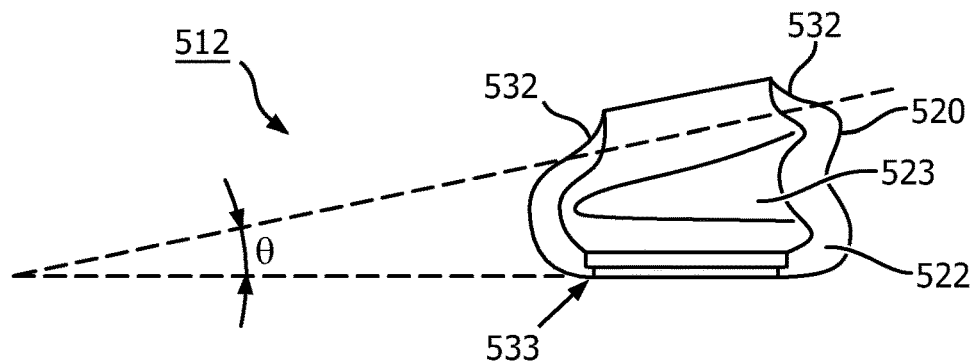
FIG. 9 is a cross-sectional view of a nasal pillow in accordance with another exemplary embodiment of the disclosed concept.

A nasal pillow 512 in accordance with yet another exemplary embodiment of the disclosed concept is shown in FIG. 9. It is contemplated that nasal pillow 512 may be used in conjunction with the patient interface device 8 shown in FIGS. 2 and 3, or with any other suitable patient interface device.

Nasal pillow 512 includes an outer casing 520 and an inner support structure 522. Nasal pillow 512 also includes nasal contact surfaces 532 and a bellows portion 523 having a multiple bellows. Similar to the nasal pillow 212 of FIG. 6, outer casing 520 and inner support structure 522 of nasal pillow 512 are pre-loaded so that nasal contact surfaces 532 are disposed at an angle θ with respect to a base portion 533 of nasal pillow 512.

In contrast with nasal pillow 212 of FIG. 6, outer casing 520 and inner support structure 522 are a unitary object rather than two separate pieces. Outer casing 520 may be overmolded onto inner support structure 522 to create the unitary object.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A nasal pillow adapted for use with a patient interface device, the nasal pillow comprising: base portion structured to interface the nasal pillow with the patient interface device, the base portion lying in a first plane;
an outer casing structured to define an interior area, the outer casing having a first upper opening defined by a first upper edge of the outer casing lying in a fourth plane, the outer casing having a first lower opening lying in the first plane; and
an inner support structure disposed in the interior area, wherein a rigidity of the inner support structure is greater than a rigidity of the outer casing, the inner support structure having a second upper opening defined by an second upper edge of the inner support structure lying in a second plane, and a second lower opening defined by a lower edge of the inner support member lying in a third plane, wherein the inner support structure is pre-loaded so that the third plane is parallel to the first plane and the second plane is disposed at an angle with respect to the first plane, wherein the second plane is not parallel with the first plane and the second plane is parallel to the fourth plane, wherein the outer casing and the inner support structure are two separate pieces, wherein the first upper opening of the outer casing is aligned with the second upper opening of the inner support structure, and wherein the first lower opening of the outer casing is aligned with the second lower opening of the inner support structure.

2. The nasal pillow of claim 1, wherein the inner support structure has a ring shape.

3. The nasal pillow of claim 1, wherein the inner support structure includes a bellows portion having a single bellows.

4. The nasal pillow of claim 1, wherein the inner support structure includes a bellows portion having a plurality of bellows.

5. The nasal pillow of claim 1, wherein the outer casing includes nasal contact surfaces structured to make contact with a sub-nasal surface of the patient.

6. The nasal pillow of claim 5, wherein the nasal contact surfaces are arranged at an angle with respect to the base portion of the nasal pillow.

7. The nasal pillow of claim 5, wherein the nasal contact surfaces are structured to make substantially flush contact with a sub-nasal surface of a patient.

8. The nasal pillow of claim 1, wherein a durometer of the outer casing is within a range of about 5 shore A to about 20 shore A.

9. The nasal pillow of claim 1, wherein a durometer of the inner support structure is within a range of about 20 shore A to about 60 shore A.

10. The nasal pillow of claim 1, wherein a material of the outer casing includes gel, silicone, foam, or rubber.

11. The nasal pillow of claim 1, wherein a material of the inner support structure includes gel, silicone, foam, or rubber.

* * * * *